United States Patent
Gogolewski

(10) Patent No.: US 6,747,121 B2
(45) Date of Patent: Jun. 8, 2004

(54) POLY(L-LACTIDE-CO-GLYCOLIDE) COPOLYMERS, METHODS FOR MAKING AND USING SAME, AND DEVICES CONTAINING SAME

(75) Inventor: Sylwester Gogolewski, Davos Platz (CH)

(73) Assignee: Synthes (USA), Paoli, PA (US)

( * ) Notice: Subject to any disclaimer, the term of this patent is extended or adjusted under 35 U.S.C. 154(b) by 0 days.

(21) Appl. No.: 09/945,704

(22) Filed: Sep. 5, 2001

(65) Prior Publication Data

US 2003/0114637 A1 Jun. 19, 2003

(51) Int. Cl.$^7$ .................. C08G 63/08; A61B 17/00; A61L 17/00; A61F 2/00
(52) U.S. Cl. .................. 528/354; 528/355; 528/359; 525/411; 525/413; 525/415; 606/65; 606/73; 606/75; 606/77; 606/151; 606/219; 606/224; 606/228; 606/230; 606/231; 606/232; 606/233; 623/1.11; 623/1.15; 623/1.38; 623/1.42
(58) Field of Search ................. 528/354, 355, 528/359; 525/411, 413, 415; 623/1.11, 1.15, 1.38, 1.42; 606/65, 73, 75, 77, 151, 219, 224, 228, 230–233, 104

(56) References Cited

U.S. PATENT DOCUMENTS

| | | | |
|---|---|---|---|
| 3,248,463 A | 4/1966 | Wiley et al. | |
| 3,531,561 A | 9/1970 | Trehu et al. | |
| 3,636,956 A | 1/1972 | Sneider | |
| 3,739,773 A | 6/1973 | Schmitt et al. | |
| 3,797,499 A | 3/1974 | Schneider | |
| 4,045,418 A | * 8/1977 | Sinclair | 156/327 |
| 4,057,537 A | * 11/1977 | Sinclair | 162/146 |
| 4,157,437 A | 6/1979 | Okuzumi et al. | 528/354 |
| 4,263,185 A | 4/1981 | Belykh et al. | |
| 4,523,591 A | 6/1985 | Kaplan et al. | |
| 4,539,981 A | 9/1985 | Tunc | |
| 4,550,449 A | 11/1985 | Tunc | |
| 4,640,271 A | 2/1987 | Lower | |
| 4,655,771 A | 4/1987 | Wallsten | |
| 4,655,777 A | 4/1987 | Dunn et al. | |
| 4,671,280 A | 6/1987 | Dorband et al. | |
| 4,743,257 A | 5/1988 | Tormala et al. | |
| 4,781,183 A | 11/1988 | Casey et al. | |
| 4,810,775 A | 3/1989 | Bendix et al. | 528/480 |
| 4,898,186 A | 2/1990 | Ikada et al. | |
| 4,905,680 A | 3/1990 | Tunc | |
| 4,924,865 A | 5/1990 | Bays et al. | |
| 4,968,317 A | 11/1990 | Tormala et al. | |
| 5,007,939 A | 4/1991 | Delcommune et al. | |
| 5,084,050 A | 1/1992 | Draenert | |
| 5,085,629 A | 2/1992 | Goldberg et al. | 604/8 |
| 5,110,852 A | * 5/1992 | Gogolewski et al. | 524/108 |
| 5,180,765 A | 1/1993 | Sinclair | |
| 5,201,738 A | 4/1993 | Scott et al. | |
| 5,223,546 A | 6/1993 | Morita et al. | 521/52 |
| 5,227,412 A | 7/1993 | Hyon et al. | |
| 5,234,652 A | 8/1993 | Woodhams et al. | |
| 5,236,431 A | * 8/1993 | Gogolewski et al. | 606/72 |
| 5,238,968 A | 8/1993 | Morita et al. | 521/79 |
| 5,319,038 A | 6/1994 | Tunc | |
| 5,322,925 A | 6/1994 | Muth et al. | 528/354 |
| 5,324,307 A | 6/1994 | Jarrett et al. | 606/219 |
| 5,359,027 A | 10/1994 | Perego et al. | 528/354 |
| 5,383,931 A | 1/1995 | Hehli et al. | |
| 5,431,652 A | 7/1995 | Shimamoto et al. | |
| 5,434,242 A | 7/1995 | Bendix et al. | 528/354 |
| 5,443,458 A | 8/1995 | Eury | |
| 5,468,253 A | * 11/1995 | Bezwada et al. | 428/395 |
| 5,475,063 A | 12/1995 | Kaplan et al. | 525/411 |
| 5,525,646 A | 6/1996 | Lundgren et al. | 523/105 |
| 5,569,250 A | 10/1996 | Sarver et al. | |
| 5,599,852 A | 2/1997 | Scopelianos et al. | 523/105 |
| 5,665,831 A | 9/1997 | Neuenschwander et al. | 525/415 |
| 5,700,901 A | 12/1997 | Hurst et al. | 528/354 |
| 5,702,717 A | * 12/1997 | Cha et al. | 424/424 |
| 5,713,920 A | * 2/1998 | Bezwada et al. | 528/357 |
| 5,714,573 A | 2/1998 | Randall et al. | 528/354 |
| 5,728,752 A | 3/1998 | Scopelianos et al. | 523/113 |
| 5,747,390 A | 5/1998 | Cooper et al. | |
| 5,747,637 A | 5/1998 | Shinoda et al. | |
| 5,792,400 A | 8/1998 | Talja et al. | |
| 5,824,247 A | 10/1998 | Tunc | |
| 5,824,333 A | 10/1998 | Scopelianos et al. | 424/423 |
| 5,827,287 A | 10/1998 | Tunc | |
| 5,968,542 A | * 10/1999 | Tipton | 424/423 |
| 6,007,539 A | 12/1999 | Kirsch et al. | |
| 6,068,920 A | 5/2000 | Funae et al. | 428/401 |

(List continued on next page.)

FOREIGN PATENT DOCUMENTS

| | | |
|---|---|---|
| DE | 42 26 465 | 2/1993 |
| EP | 0 202 090 | 11/1986 |
| EP | 0 321 176 | 6/1989 |
| EP | 0 349 656 | 1/1990 |
| EP | 401 844 | 12/1990 |
| EP | 460 439 | 12/1991 |
| EP | 1 034 806 | 9/2000 |
| WO | WO 80/02641 | 12/1980 |
| WO | WO 88/05312 | 7/1988 |
| WO | WO 89/01767 | 3/1989 |
| WO | WO 90/04982 | 5/1990 |
| WO | WO 92/15342 | 9/1992 |
| WO | WO 95/26762 | 10/1995 |
| WO | WO 97/36553 | 10/1997 |
| WO | WO 00/1307 | 1/2000 |

*Primary Examiner*—P. Hampton Hightower
(74) *Attorney, Agent, or Firm*—Jones Day

(57) ABSTRACT

The present invention relates in general to implantable, resorbable copolymers containing L-lactide and glycolide repeat units, and in particular to terpolymers containing L-lactide, glycolide, and one other type of repeat unit selected from the group consisting of D-lactide, D,L-lactide, and ε-caprolactone. Medical devices for in vivo implantation applications containing such implantable, resorbable copolymers are also described, as well as methods for making such copolymers and devices.

34 Claims, No Drawings

U.S. PATENT DOCUMENTS

| | | |
|---|---|---|
| 6,096,855 A | 8/2000 | Sodergard et al. .......... 528/354 |
| 6,171,338 B1 | 1/2001 | Talja et al. |
| 6,206,883 B1 | 3/2001 | Tunc |
| 6,221,075 B1 | 4/2001 | Tormala et al. |
| 6,227,927 B1 | 5/2001 | Smith |
| 6,228,954 B1 | 5/2001 | Kaplan et al. .............. 525/411 |
| 6,235,869 B1 | 5/2001 | Roby et al. ................. 528/354 |
| 6,245,345 B1 * | 6/2001 | Swanbom et al. .......... 424/402 |
| 6,277,927 B1 | 8/2001 | Roby et al. ................. 525/411 |
| 6,325,810 B1 * | 12/2001 | Hamilton et al. ........ 227/175.1 |
| 2001/0021871 A1 | 9/2001 | Stinson |

* cited by examiner

POLY(L-LACTIDE-CO-GLYCOLIDE) COPOLYMERS, METHODS FOR MAKING AND USING SAME, AND DEVICES CONTAINING SAME

FIELD OF THE INVENTION

The present invention relates in general to implantable, resorbable copolymers containing L-lactide and glycolide repeat units, and in particular to terpolymers containing L-lactide, glycolide, and one other type of repeat unit selected from the group consisting of D-lactide, D,L-lactide, and ε-caprolactone. Medical devices for in vivo implantation applications containing such implantable, resorbable copolymers are also described, as well as methods for making such copolymers and devices.

BACKGROUND OF THE INVENTION

There is a wealth of information regarding the utility of polylactides, polyglycolides, and other resorbable materials, particularly pertaining to resorbable implants. These resorbable implants, as compared to traditional, non-resorbable metal or composite implants, for example, have the advantage of being biocompatible, of being biodegradable after a period of time, and of not requiring removal, e.g., in bone fixation or repair applications.

Copolymers containing resorbable materials can be made as well. Certain varieties of these copolymers have been made and described in the following publications.

U.S. Pat. Nos. 5,223,546 and 5,238,968 describe polymer networks based on a foam formed from the combination of a foaming agent, a poly(lactic acid)-base resin, and an optional plasticizer. The poly(lactic acid)-base resin may comprise a polymer made of lactic acid or a lactic acid-hydroxycarboxylic acid copolymer.

U.S. Pat. No. 5,236,431 describes a resorbable fixation device useful for treating torn bodily material in vivo. This fixation device, according to the disclosure, can contain resorbable copolymers made from a variety of possible monomers, including highly purified polyhydroxyacids such as lactides and gylcolide.

U.S. Pat. No. 5,322,925 describes surgical articles made from absorbable polymers. The absorbable polymers of this disclosure are block copolymers of one type or another, containing various combinations of lactide, glycolide, and/or trimethylene carbonate in the block segments.

U.S. Pat. No. 5,599,852 discloses injectable, bioabsorbable microdispersions including liquid polymers for tissue augmentation and repair. The liquid polymers of this disclosure contain a first set of repeating units from lactones including caprolactone, trimethylene carbonate, ether lactones, or combinations thereof, and a second set of repeating units including lactides, glycolides, p-dioxanone, or combinations thereof.

SUMMARY OF THE INVENTION

The invention primarily relates to terpolymers having repeat units of L-lactide, glycolide, and either D,L-lactide, D-lactide, or ε-caprolactone, as well as implantable and/or resorbable medical devices containing such terpolymers. The implantable and/or resorbable medical devices containing such terpolymers may advantageously be fabricated into the form of a bone fixation plate, screw, tack, clip, staple, pin, rod, anchor, scaffold, sponge, implant for cell encapsulation, implant for tissue engineering, drug delivery device, monofilament or multifilament structure, sheet, membrane, and a foamed article.

In one embodiment, the terpolymer contains from about 75% to about 90% L-lactide repeat units, from about 4% to about 11% D-lactide repeat units, and from about 4% to about 18% glycolide repeat units. In a preferred embodiment, the terpolymer consists essentially of about 90% L-lactide repeat units, about 5% D-lactide repeat units, and about 5% glycolide repeat units. In another preferred embodiment, the terpolymer consists essentially of about 85% L-lactide repeat units, about 5% D-lactide repeat units, and about 10% glycolide repeat units.

In another embodiment, the terpolymer contains at least about 50% L-lactide repeat units, from about 1% to about 20% repeat units from ε-caprolactone, and from about 1% to about 30% glycolide repeat units. In a preferred embodiment, the terpolymer consists essentially of about 80% L-lactide repeat units, about 10% repeat units from ε-caprolactone, and about 10% glycolide repeat units.

In still another embodiment, the terpolymer contains at least about 50% L-lactide repeat units, from about 1% to about 20% D,L-lactide repeat units, and from about 1% to about 30% glycolide repeat units. In a preferred embodiment, the terpolymer consists essentially of about 80% L-lactide repeat units, about 10% D,L-lactide repeat units, and about 10% glycolide repeat units. In another preferred embodiment, the terpolymer consists essentially of about 80% L-lactide repeat units, about 5% D,L-lactide repeat units, and about 15% glycolide repeat units.

In yet another embodiment, from about 1% to about 20% of the repeat units of the terpolymer are D-lactide repeat units; preferably, from about 4% to about 11% of the repeat units of the terpolymer are D-lactide repeat units. In another embodiment, from about 50% to about 95% of the repeat units of the terpolymer are L-lactide repeat units; preferably, from about 75% to about 90% of the repeat units of the terpolymer are L-lactide repeat units. In another embodiment, from about 1% to about 30% of the repeat units of the terpolymer are glycolide repeat units; preferably, from about 4% to about 18% of the repeat units of the terpolymer are glycolide repeat units.

The terpolymer may also be expressed as having repeat units depicted by the following formula:

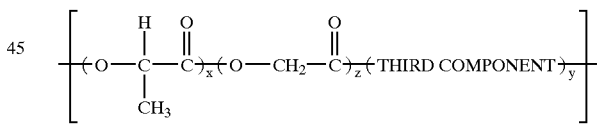

wherein the repeat unit having subscript x is an L-lactide repeat unit, the third component having subscript y is either a D-lactide repeat unit, a D,L-lactide repeat unit, or a repeat unit based on a ring-opened ε-caprolactone structure. Advantageously, the molar percentages of the repeating units are such that x is from about 0.75 to about 0.9, y is from about 0.02 to about 0.16, z is from about 0.04 to about 0.18, and x+y+z=1.

In one embodiment, x is from about 0.75 to about 0.9, y is from about 0.04 to about 0.11, and z is from about 0.05 to about 0.15. In a preferred embodiment, x is essentially about 0.85, y is essentially about 0.05, and z is essentially about 0.1. In another preferred embodiment, x is essentially about 0.9, y is essentially about 0.05, and z is essentially about 0.05.

Another aspect of the invention relates to implantable medical devices that contain any of the terpolymers listed above.

In one embodiment, the terpolymers can be made by a process that includes combining L-lactic acid monomer, from about 2% to about 16% of D-lactic acid monomer, and glycolic acid monomer to form a monomer mixture and polymerizing substantially all of the monomer mixture to form the terpolymer.

In another embodiment, the terpolymer can be made by a process that includes combining L-lactide dimer, D-lactide dimer, and glycolide dimer to form a dimer mixture and polymerizing substantially all of the dimer mixture to form the terpolymer.

In yet another embodiment, the terpolymer can be made by a process that includes contacting a combination of monomers and dimers that correspond to repeat unit structures of L-lactide, D-lactide, and glycolide to form a monomer-dimer mixture and polymerizing substantially all of the monomer-dimer mixture to form the terpolymer.

In still another embodiment, the terpolymer can be made by a process that includes combining L-lactide dimer, D,L-lactide dimer, and glycolide dimer to form a dimer mixture and polymerizing substantially all of the dimer mixture to form the terpolymer.

In another embodiment, the terpolymer can be made by a process that includes contacting a combination of monomers and dimers that correspond to repeat unit structures of L-lactide, D,L-lactide, and glycolide to form a monomer-dimer mixture and polymerizing substantially all of the monomer-dimer mixture to form the terpolymer.

In another embodiment, the terpolymer can be made by a process that includes combining L-lactic acid monomer, $\epsilon$-caprolactone monomer, and glycolic acid monomer to form a monomer mixture and polymerizing substantially all of the monomer mixture to form the terpolymer.

In another embodiment, the terpolymer can be made by a process that includes contacting a combination of monomers and dimers that correspond to repeat unit structures of L-lactide, a ring-opened ester from $\epsilon$-caprolactone, and glycolide to form a monomer-dimer mixture and polymerizing substantially all of the monomer-dimer mixture to form the terpolymer.

DETAILED DESCRIPTION OF THE PREFERRED EMBODIMENTS

Poly(L-lactide-co-glycolide) copolymers according to the present invention are typically meant to be used in bioabsorbable applications, implantable medical devices, and the like. Specifically, such applications or devices may include, but are not limited to, bone fixation plates (e.g., maxillofacial, orthopaedic, or the like), screws, tacks, clips, staples, pins or rods, anchors (e.g., for suture, bone, or the like), scaffolds, sponges, implants for cell encapsulation or tissue engineering, drug delivery (e.g., carriers, etc.), monofilament or multifilament structures, sheets, membranes (e.g., porous, microporous, etc.), foams (e.g., open cell or closed cell), or combinations thereof.

The poly(L-lactide-co-glycolide) copolymers of the present invention contains: L-lactide dimer or L-lactic acid monomer repeat units; and glycolide dimer or glycolic acid repeat units in the copolymer. Whether the repeat units are from depending upon the polymerization process used to form these copolymers.

Preferably, a third type of repeat unit is present in the poly(L-lactide-co-glycolide) copolymers according to the present invention selected from the group consisting of D-lactide dimer, D,L-lactide (or meso-lactide) dimer, the ring-opened structure of $\epsilon$-caprolactone (or pentamethylene carboxylate ester) monomer, or D-lactic acid monomer, again depending upon the polymerization process used to form these copolymers.

Other types of resorbable and/or biocompatible monomers or dimers may optionally be present as repeat units in the copolymers according to the present invention. Such suitable other monomers or dimers include, for example, but are not limited to, $\alpha$-hydroxy acids, such as $\alpha$-hydroxybutyric acid, $\alpha$-hydroxyvaleric acid, $\alpha$-hydroxyacetic acid, $\alpha$-hydroxycaproic acid, $\alpha$-hydroxyheptanoic acid, $\alpha$-hydroxydecanoic acid, $\alpha$-hydroxymyristic acid, $\alpha$-hydroxyoctanoic acid, $\alpha$-hydroxystearic acid, or the like, adducts thereof, dehydration product dimers thereof, or derivatives thereof, or mixtures thereof; lactide or lactic acid adducts or derivatives, such as $\beta$-propiolactide or $\beta$-propiolactic acid, or mixtures thereof; other cyclic, linear, or branched esters, such as $\gamma$-caprolactone, $\beta$-caprolactone, $\gamma$-butyrolactone, pivalolactone, or the like, glycolide or glycolic acid adducts or derivatives, such as tetramethylglycolide, tetramethylglycolic acid, dimethylglycolic acid, or the like, or mixtures thereof; or combinations or mixtures thereof.

These poly(L-lactide-co-glycolide) copolymers are typically linear or only lightly branched, grafted, or crosslinked (i.e., at least about 98%, preferably at least about 99%, of the monomers or dimers are located on a linear polymer backbone and not in a branch or graft side chain or in a crosslink connector chain). However, if desired, the molecular architecture of the poly(L-lactide-co-glycolide) copolymers according to the invention may optionally be altered to be substantially non-linear, e.g., to contain short- or long-chain branches, to contain heterologous graft chains, to contain at least about 2% crosslinking, to form comb copolymers, to form dendritic copolymers, or the like, or combinations thereof.

The poly(L-lactide-co-glycolide) copolymers of the present invention may advantageously be made by polymerizing the various types of acid dimers (i.e., L-lactide, D-lactide, D,L-lactide, glycolide, or other optional dehydration product acid dimers, or combinations thereof), along with any desired cyclic ester monomers, if present. Alternatively, the poly(L-lactide-co-glycolide) copolymers of the present invention may be made by polymerizing only monomeric forms of the biocompatible acids mentioned above (i.e., L-lactic acid, D-lactic acid, glycolic acid, or other optional acid monomers, or combinations thereof) and of the desired cyclic ester monomers, if present. In yet another alternative embodiment, the poly(L-lactide-co-glycolide) copolymers of the present invention may be made from some mixture of monomeric (i.e., L-lactic acid, D-lactic acid, glycolic acid, or other optional acid monomers, or combinations thereof) and dimeric forms (i.e., L-lactide, D-lactide, D,L-lactide, glycolide, or other optional dehydration product acid dimers, or combinations thereof) of the resorbable components mentioned above and of the desired cyclic esters, if present.

Any polymerization method capable of forming a polylactide or polyglycolide copolymer may be utilized to make the poly(L-lactide-co-glycolide) copolymers of the present invention, particularly any method capable of forming the copolymer such that the biodegradation or resorbability and the mechanical properties (e.g., before and during implantation) are sufficient for the requirements of the application for which the copolymer is to be used. For example, one such polymerization method may be found in U.S. Pat. No. 6,096,855, the entire disclosure of which is incorporated herein by reference hereto. Other examples of copolymerizations method for producing poly(D,L-lactideco-glycolide) and other random copolymers of resorbable materials are disclosed in U.S. Pat. No. 4,157,437 and International Publication No. WO 97/36553, the entire disclosures of which are also incorporated herein by reference hereto.

Water and/or an organic solvent (or a mixture of organic solvents), or a mixture thereof, may be used in a polymerization method, e.g., a solution polymerization, according to the invention to form the described poly(L-lactide-co-glycolide) copolymers, or they made be made in a bulk polymerization. Reaction temperature may be adjusted to suit the polymerization method; e.g., it may be at or below room temperature or at increased temperatures, whether to maintain a melt when no solvent is present or to activate an initiator or to sustain an appreciable propagation rate or for some other reason. Catalysts, initiators, co-initiators, chain termination suppressing agents, stabilization additives, and other components may also be added to the polymerization reaction according to the invention in any amounts necessary to facilitate formation of the poly(L-lactide-co-glycolide) copolymers of the invention. In one embodiment, the poly(L-lactide-co-glycolide) copolymers, as well as any medical devices or surgical articles made therefrom, do not contain any added chain extenders (i.e., compounds that have groups that can react at sites on the repeat units of the poly(L-lactide-co-glycolide) copolymers to increase the molecular weight or to induce branching, grafting, or crosslinking more than about 2%). In another embodiment, the poly(L-lactide-co-glycolide) copolymers, as well as any medical devices or surgical articles made therefrom, do not contain any added foaming agents (e.g., organic or inorganic agents that may intramolecularly release a gas or react with another molecule of the same kind to release a gas).

These poly(L-lactide-co-glycolide) copolymers according to the invention preferably exhibit as close to a statistically random distribution of monomeric or dimeric repeat units as possible, taking into consideration the possible effect of the differences in reactivity ratios between the respective monomers or dimers. Nevertheless, there may be some alternating, blocky, or other non-random character in arrangement of the repeat units of the poly(L-lactide-co-glycolide) copolymers according to the present invention that may stem from such reactivity ratio differences.

Preferred poly(L-lactide-co-glycolide) copolymer compositions according to the invention are terpolymers (i.e., are copolymers that contain three different types of monomeric/dimeric repeat units) and include those made from a majority (at least 50 mol %) of L-lactide component, but preferably not more than about 95 mol %. More preferably, about 75 mol % to about 90 mol % of the repeat units of the terpolymers are L-lactide repeat units. Such preferred terpolymer compositions also contain from about 1 mol % to about 30 mol % of glycolide component, preferably from about 2 mol % to about 24 mol %, more preferably from about 4 mol % to about 18 mol %, most preferably from about 5 mol % to about 15 mol %. The ranges of values equally apply whether there are only two components or a third component is present.

In a more preferred embodiment, the poly(L-lactide-co-glycolide) copolymer compositions according to the invention contain from about 1 mol % to about 20 mol % of a third monomeric or dimeric component, when present, preferably from about 2 mol % to about 16 mol %, more preferably from about 3 mol % to about 13 mol %, most preferably from about 4 mol % to about 11 mol %. In such an embodiment, the third monomeric or dimeric component in the terpolymer is one of D-lactide, D,L-lactide, ε-caprolactone, or D-lactic acid.

The terpolymers of the present invention may also be expressed as having repeat units depicted by the following formula:

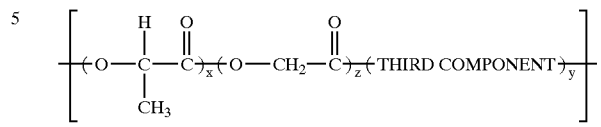

wherein the repeat unit having subscript x is an L-lactide repeat unit, the third component having subscript y is either a D-lactide repeat unit, a D,L-lactide repeat unit, or a repeat unit based on a ring-opened ε-caprolactone structure. In such a case, the subscripts x, y, and z represent the relative percentages for each component described above and, when these relative percentages are totaled, should add up to 1.

In one embodiment, the poly(L-lactide-co-glycolide) copolymer according to the invention contains repeat units of L-lactide, D-lactide, and glycolide, whether from all monomers, all dimers, or a mixture thereof. For instance, the poly(L-lactide-co-glycolide) copolymer according to the invention may be made from a mixture of: L-lactic acid, D-lactic acid, and glycolic acid; L-lactic acid, D-lactic acid, and glycolide dimer; L-lactic acid, D-lactide dimer, and glycolic acid; L-lactide dimer, D-lactic acid, and glycolic acid; L-lactic acid, D-lactide dimer, and glycolide dimer; L-lactide dimer, D-lactic acid, and glycolide dimer; L-lactide dimer, D-lactide dimer, and glycolic acid; or L-lactide dimer, D-lactide dimer, and glycolide dimer. Alternately, one or more components of this terpolymer may include a mixture of the monomeric and dimeric forms, e.g., a mixture of L-lactic acid and L-lactide dimer, D-lactide dimer, and glycolide dimer, a mixture of L-lactide dimer, D-lactic acid and D-lactide dimer, and glycolide dimer, etc.

In another embodiment, the poly(L-lactide-co-glycolide) copolymer according to the invention contains repeat units of L-lactide, D,L-(or meso-) lactide, and glycolide, whether from all dimers or a mixture of monomers and dimers. For instance, the poly(L-lactide-co-glycolide) copolymer according to the invention may be made from a mixture of: L-lactic acid, D,L-lactide dimer, and glycolic acid; L-lactic acid, D,L-lactide dimer, and glycolide dimer; L-lactide dimer, D,L-lactide dimer, and glycolic acid; or L-lactide dimer, D,L-lactide dimer, and glycolide dimer. Alternately, one or more components of this terpolymer (aside from the D,L-lactide dimer) may include a mixture of the monomeric and dimeric forms, e.g., a mixture of L-lactic acid and L-lactide dimer, D,L-lactide dimer, and glycolide dimer, a mixture of L-lactide dimer, D,L-lactide dimer, and glycolic acid and glycolide dimer, etc.

In still another embodiment, the poly(L-lactide-co-glycolide) copolymer according to the invention contains repeat units of L-lactide, ε-caprolactone, and glycolide, whether from all monomers or a mixture of monomers and dimers. For instance, the poly(L-lactide-co-glycolide) copolymer according to the invention may be made from a mixture of: L-lactic acid, ε-caprolactone monomer, and glycolic acid; L-lactic acid, ε-caprolactone monomer, and glycolide dimer; L-lactide dimer, ε-caprolactone monomer, and glycolic acid; or L-lactide dimer, ε-caprolactone monomer, and glycolide dimer. Alternately, one or more components of this terpolymer (aside from the ε-caprolactone monomer) may include a mixture of the monomeric and dimeric forms, e.g., a mixture of L-lactic acid and L-lactide dimer, ε-caprolactone monomer, and glycolide dimer, a mixture of L-lactide dimer, ε-caprolactone monomer, and glycolic acid and glycolide dimer, etc.

When present, the amount of other types of optional resorbable and/or biocompatible monomers or dimers in the poly(L-lactide-co-glycolide) composition of the copolymers of the invention can advantageously be less than about 15 mol %, preferably less than about 12 mol %, or alternately from about 1 mol % to about 11 mol % or from about 4 mol % to 10 mol % or from about 1 mol % to about 5 mol %.

Advantageously, the poly(L-lactide-co-glycolide) copolymers according to the invention, whatever their method of polymerization, must have a sufficient molecular weight to be able to perform (e.g., mechanically) in the desired application. Generally, a sufficiently high molecular weight can be obtained by polymerizing substantially all (i.e., preferably at least about 98 mol %, more preferably at least about 99 mol %, most preferably at least about 99.5 mol %) of the monomeric and/or dimeric copolymer substituents. As used herein, the term "molecular weight" should be understood to mean extent of polymerization, or number or weight average of monomeric or dimeric units in the copolymer chains. Molecular weight, as used herein, may be approximated by a number of known methods, e.g., such as by gel permeation or size exclusion chromatography (GPC or SEC), by inherent or intrinsic viscosity analysis (I.V.), or by an equivalent scientific technique through which a correlation may be made to estimate copolymer molecular weight.

When measured by GPC or SEC against polystyrene standards, the poly(L-lactide-co-glycolide) copolymers according to the invention (before being processed or fabricated into a shaped article for a desired application) should preferably exhibit a number average molecular weight of at least about 75,000 grams/mole, more preferably from about 150,000 grams/mole to about 1,000,000 grams/mole, most preferably from about 250,000 grams/mole to about 900,000 grams/mole. Such measurements should preferably also yield a weight average molecular weight of at least about 125,000 grams/mole, more preferably at least about 250,000 grams/mole, most preferably from about 400,000 grams/mole to about 2,500,000 grams/mole. Alternately, in some embodiments, the number average molecular weight may be between about 16,000 grams/mole and about 75,000 grams/mole or between about 18,000 grams/mole and about 50,000 grams/mole, and the number average molecular weight may be between about 50,000 grams/mole and about 150,000 grams/mole or between about 60,000 grams/mole and about 120,000 grams/mole. Such measurements should also generally show a polydispersity (i.e., a ratio of weight average molecular weight to number average molecular weight) from about 1.3 to about 3.5, preferably from about 1.6 to about 2.8, more preferably from about 1.85 to about 2.5. However, the desired application for which the poly(L-lactide-co-glycolide) copolymer will be used should generally determine the acceptable range of molecular weight values, e.g., a copolymer used for drug delivery, maxillofacial implant, or other application in which enhanced biodegradation or resorbability is paramount, may be preferred to exhibit number average and/or weight average molecular weights in a lower region of, or even below, the ranges listed above, whereas a copolymer used in a pin, rod, anchor, staple, or other mechanically-intensive and/or load-bearing application may be preferred to exhibit number average and/or weight average molecular weights in an intermediate or upper region of, or even above, the ranges listed above.

When measured for I.V. at a concentration of about 0.1% w/v in chloroform, the poly(L-lactide-co-glycolide) copolymers according to the invention (before being processed or fabricated into a shaped article for a desired application) should generally exhibit an inherent viscosity of at least about 1.0 dL/g, preferably from about 2.5 dL/g to about 8 dL/g, more preferably from about 3 dL/g to about 7 dL/g, most preferably from about 4 dL/g to about 6.5 dL/g. In one embodiment, the inherent viscosity of the poly(L-lactide-co-glycolide) copolymer of the invention is greater than about 4.5 dL/g. However, the desired application for which the poly(L-lactide-co-glycolide) copolymer will be used should generally determine the acceptable range of inherent viscosity values, e.g., a copolymer used for drug delivery, maxillofacial implant, or other application in which enhanced biodegradation or resorbability is paramount, may be preferred to exhibit lower inherent or intrinsic viscosities than those listed above, whereas a copolymer used in a pin, rod, anchor, staple, or other mechanically-intensive and/or load-bearing application may be preferred to exhibit inherent or intrinsic viscosities within, or even above, those listed above.

The copolymers according to the invention should also contain a low monomer and/or dimer concentration and a low solvent concentration. Preferably at least one is less than about 1%, more preferably less than about 0.5%, most preferably less than about 0.2%, by weight. Further, the poly(L-lactide-co-glycolide) copolymers according to the invention must have a low moisture (or water) content, for example, not more than about 1.5%, preferably not more than about 1%, by weight. When the poly(L-lactide-co-glycolide) copolymer is to be formed into an article or device for a particular application, it is preferred that the moisture or water content is not more than about 500 ppm, more preferably not more than about 250 ppm, most preferably not more than about 150 ppm. In other very preferred embodiments, the moisture or water content of a poly(L-lactide-co-glycolide) copolymer according to the invention that is being formed into an article or device according to the invention is not more than about 200 ppm, or not more than about 100 ppm.

In some circumstances, the poly(L-lactide-co-glycolide) copolymers according to the invention may be subject to a drying and/or volatile organic compound (VOC) removal step, in order to remove water, organic solvent(s), unreacted monomer/dimer, or other low molecular weight and/or volatile impurities or compounds that may be present in the poly(L-lactide-co-glycolide) copolymers. This drying/removal step may include, but is not limited to, introduction of a relatively-dry, inert gas (e.g., such as dry nitrogen, argon, or the like, or a mixture containing such a gas), application of a vacuum (e.g., such that the pressure is not more than about 10 Torr, preferably not more than about 5 Torr, more preferably not more than about 1 Torr), application of an increased temperature (e.g., of at least about 50° C., preferably at least about 65° C., more preferably from about 70° C. to about 120° C., and also preferably, provided that the copolymer is at least partially crystalline, that the increased temperature is not greater than about 5° C. below its melting temperature, preferably not greater than about 10° C. below its melting temperature), or any combination thereof. This drying/removal step is generally undertaken for a period of time sufficient to render the moisture content within acceptable or preferred limits. When performed, the step may advantageously include a combination of application of increased temperature and application of a vacuum and occurs for at least about 4 hours, preferably for at least about 12 hours, or alternately for not more than about 24 hours or from about 16 hours to about 20 hours.

The poly(L-lactide-co-glycolide) copolymers according to the present invention can exhibit a wide range of degrees of crystallinity, with preferable values depending upon the desired application for which they are to be used. In one preferred embodiment, the poly(L-lactide-co-glycolide) copolymers of the invention are semicrystalline and typically exhibit a degree of crystallinity from about 15% to about 30%, preferably from about 20% to about 30%, more preferably from about 20% to about 26%. In another preferred embodiment, the poly(L-lactide-co-glycolide) copolymers of the invention can exhibit a degree of crystallinity of less than about 15%. In an alternate embodiment, the poly(L-lactide-co-glycolide) copolymers of the invention can exhibit a degree of crystallinity from about 15% to about 50%. In other alternate embodiments, the poly(L-lactide-co-glycolide) copolymers of the invention can exhibit a degree of crystallinity of less than about 10%, less than about 5%, less than about 1%, or may exhibit substantially no crystallinity (i.e., less than about 0.5%, preferably less than about 0.1%, or at any rate not quantitatively detectable by one or more experimental methods). The "degree of crystallinity" can be measured by a number of well-known experimental techniques and, when the term is used herein, reflects the relative proportion, by volume, cross-sectional area, or linear path through a sample, of crystalline regions in comparison to non-crystalline or amorphous regions of the poly(L-lactide-co-glycolide) copolymer. Suitable experimental techniques to measure degree of crystallinity include, but are not limited to, differential scanning calorimetry (DSC), x-ray scattering or diffraction methods (e.g. XRD, WAXD, WAXS, etc.), or the like.

The poly(L-lactide-co-glycolide) copolymers according to the present invention can also exhibit a wide range of degrees of crystalline perfection (or crystalline imperfection), again with preferable values depending upon the desired application for which they are to be used. The degree of crystalline perfection or imperfection can be measured, for example, by DSC or another well-known experimental technique and can be referred to herein in terms of a heat of fusion ($\Delta H_f$), which represents the relative perfection or imperfection of the crystals of the copolymer in terms of the amount of energy per unit of material (e.g., in Joules per gram, J/g, or millijoules per milligram, mJ/mg) required to melt, or de-crystallize, the crystals of the copolymer. In one preferred embodiment, the poly(L-lactide-co-glycolide) copolymers of the invention are semicrystalline and typically exhibit a heat of fusion of less than about 50 J/g, preferably less than about 30 J/g, more preferably less than about 25 J/g. In another preferred embodiment, the poly(L-lactide-co-glycolide) copolymers of the invention can exhibit a heat of fusion from about 50 J/g to about 70 J/g. In alternate preferred embodiments, the poly(L-lactide-co-glycolide) copolymers of the invention can exhibit a heat of fusion of from about 0.5 J/g to about 15 J/g, from about 0.1 J/g to about 10 J/g, from about 15 J/g to about 25 J/g, or may exhibit substantially no heat of fusion (i.e., less than about 0.1 J/g, or at any rate not quantitatively detectable by one or more experimental methods).

Melting temperatures and glass transition temperatures for the poly(L-lactide-co-glycolide) copolymers according to the present invention can also vary widely, with preferable values depending upon the desired application for which they are to be used. Melting and glass transition temperatures may be measured, for example, by DSC or another well-known experimental technique, and are generally dependent upon the rate at which temperature is increased or decreased. Standard DSC tests are performed with temperature changing at a rate of about 5° C./min to about 20° C./min, particularly at about 10° C./min. When present, the melting temperature of the poly(L-lactide-co-glycolide) copolymers of the present invention, as measured by standard DSC tests, is generally between about 90° C. and about 165° C., preferably from about 110° C. to about 155° C., more preferably from about 130° C. to about 150° C. The glass transition temperatures of the poly(L-lactide-co-glycolide) copolymers of the present invention, as measured by standard DSC tests, is generally between about 30° C. and about 100° C., preferably between about 40° C. and about 60° C.

While preferably values may vary widely, depending inter alia upon the desired application for which they are to be used and the process by which they are formed into articles or devices for said applications, the poly(L-lactide-co-glycolide) copolymers according to the present invention may generally exhibit mechanical properties within the following ranges:

| MECHANICAL PROPERTY | RANGE OF VALUES |
| --- | --- |
| Flexural Modulus | about 3 to about 14 GPa |
| Flexural Strength | about 160 to about 200 MPa |
| Tensile Modulus (secant to 0.2% strain) | about 5 to about 9 GPa |
| Tensile Strength | about 125 to about 175 MPa |
| Shear Strength | about 90 to about 175 MPa |

When the poly(L-lactide-co-glycolide) copolymers according to the invention are processed using non-orienting techniques, e.g., such as by melt casting, solution casting, compression molding, or the like, their mechanical properties may be in the lower end of some of the ranges, or may even be below some of the ranges, listed above. When the poly(L-lactide-co-glycolide) copolymers according to the invention are processed using orienting techniques, e.g., such as by melt extrusion, solid state extrusion, hot rolling, cold rolling, injection molding, or the like, their mechanical properties may advantageously be in the intermediate to upper portion of some of the ranges, or may even be above some of the ranges, listed above. The type of processing used will generally at least partially depend on the mechanical properties desired in the application for which the poly(L-lactide-co-glycolide) copolymers or devices containing them are to be used.

As the poly(L-lactide-co-glycolide) copolymers or devices according to the invention have utility in implantations and in vivo applications, it may be desirable to sterilize such copolymers and/or devices to minimize in vivo response, e.g., from infection, foreign body rejection, or the like. Because the poly(L-lactide-co-glycolide) copolymers of the invention are degradable in the presence of water, sterilization methods other than autoclaving are particularly appropriate. Such sterilization may include, but are not limited to, exposure to ethylene oxide, exposure to γ-radiation, exposure to an electron beam source, exposure to a cold (or at least low-temperature) plasma source, or a combination thereof. The sterilization process, depending upon the exposure dose and duration, may be one possible way to introduce branching, grafting, or crosslinking to the poly(L-lactide-co-glydolide) copolymers of the present invention or devices containing same.

Single or multiple doses to these means of sterilization may be performed on the copolymers, articles, or devices according to the invention in an amount, or in amounts, sufficient to prevent, inhibit, or curtail in vivo response. In one preferred embodiment, the sterilization includes a single dose exposure to γ-radiation or ethylene oxide. In another preferred embodiment, the sterilization includes a single dose exposure of the poly(L-lactide-co-glycolide) copolymers or devices according to the invention to γ-radiation of 25 kGy.

When forming devices containing the poly(L-lactide-co-glycolide) copolymers according to the invention, e.g., such as for applications listed herein above, the poly(L-lactide-co-glycolide) copolymers can be obtained by the polymerization methods described herein and/or known in the art, optionally purified (e.g., by a method such as that disclosed in U.S. Pat. No. 4,810,775, the entire disclosure of which is incorporated herein by reference hereto), optionally treated to dry and/or remove volatile compounds from the copolymers to within specified limits of the particular application for which the device is to be used, processing the poly(L-lactide-co-glycolide) copolymer by an orienting technique or by a non-orienting technique into a desired shape or device, optionally further processing the desired shape to induce or confer (further) orientation and to form a device, optionally treating the device to remove or to reduce any stress concentrations present in the device, and optionally but preferably sterilizing the device.

If desired, poly(L-lactide-co-glycolide) copolymers according to the present invention may optionally be physically mixed, admixed, and/or blended with a homopolymer of one or more of the types of repeat units in said copolymer or with a second copolymer containing at least one of the types of repeat units in said poly(L-lactide-co-glycolide) copolymer according to the invention. Preferably, this physical mixture, admixture, or blend will be performed before processing of the poly(L-lactide-co-glycolide) copolymer according to the invention into a desired shape or an article or device according to the invention. The homopolymer or copolymer may be added to the poly(L-lactide-co-glycolide) copolymer according to the invention by any traditional means known to those in the art, e.g., such as by mechanical mixers in the melt or solid state, by dissolving together in an appropriate solvent (mixture) and then sufficiently removing the solvent (mixture), by a similar technique, or by a combination thereof. When an additional homopolymer or copolymer is added in this way, it is typically present in an amount less than about 10% by weight of the poly(L-lactide-co-glycolide) copolymer according to the invention, alternately less than about 5% or less than about 2%.

Poly(L-lactide-co-glycolide) copolymers or devices containing them tend to exhibit complete in vivo or in vitro resorption from about 9 months to about 2.5 years, preferably from about 1 year to about 2 years. As used herein, "complete resorption" refers to the situation where, upon visual inspection, there is either no evidence of poly(L-lactide-co-glycolide) copolymeric material at the site of implantation, or where, upon analysis of a sample of the implantation site of the degraded copolymer, there is an absence of oligomeric material resultant from degradation of the poly(L-lactide-co-glycolide) copolymer that has a number average molecular weight of more than about 1,000 grams/mole, preferably not more than about 500 grams/mole.

In addition, the poly(L-lactide-co-glycolide) copolymers or devices according to the invention should typically retain at least a portion of their mechanical properties after implantation in vivo or after exposure to a phosphate buffered saline (PBS) solution having a pH of about 7.4 (±0.2) at a temperature of about 37° C. (±1° C.).

In one embodiment, upon exposure to PBS solution in vitro for about 12 weeks, an implantable medical device containing a poly(L-lactide-co-glycolide) copolymer according to the invention may retain: not more than about 25% of its flexural modulus, preferably not more than about 10%, more preferably essentially none of its flexural modulus (i.e., it was not measurable); not more than about 25% of its flexural strength, preferably not more than about 10%, more preferably essentially none of its flexural strength (i.e., it was not measurable); not more than about 25% of its tensile strength, preferably not more than about 10%, more preferably essentially none of its tensile strength (i.e., it was not measurable); not more than about 25% of its shear strength, preferably not more than about 20%, alternately at least about 10% of its shear strength; or a combination thereof.

In another embodiment, upon exposure to PBS solution in vitro for about 20 weeks, an implantable medical device containing a poly(L-lactide-co-glycolide) copolymer according to the invention may retain: not more than about 25% of its flexural modulus, preferably not more than about 10%, more preferably essentially none of its flexural modulus (i.e., it was not measurable); not more than about 25% of its flexural strength, preferably not more than about 10%, more preferably essentially none of its flexural strength (i.e., it was not measurable); not more than about 25% of its tensile strength, preferably not more than about 10%, more preferably essentially none of its tensile strength (i.e., it was not measurable); not more than about 25% of its shear strength, preferably not more than about 20%, more preferably essentially none of its shear strength (i.e., it was not measurable); or a combination thereof.

In another embodiment, upon exposure to PBS solution in vitro for about 36 weeks, an implantable medical device containing a poly(L-lactide-co-glycolide) copolymer according to the invention may retain: not more than about 25% of its flexural modulus, preferably not more than about 10%, more preferably essentially none of its flexural modulus (i.e., it was not measurable); not more than about 25% of its flexural strength, preferably not more than about 10%, more preferably essentially none of its flexural strength (i.e., it was not measurable); not more than about 25% of its tensile strength, preferably not more than about 10%, more preferably essentially none of its tensile strength (i.e., it was not measurable); not more than about 25% of its shear strength, preferably not more than about 10%, more preferably not more than about 2%; or a combination thereof.

In yet another embodiment, upon exposure to PBS solution in vitro for about 20 weeks, an implantable medical device containing a poly(L-lactide-co-glycolide) copolymer according to the invention may retain: at least about 50% of its flexural modulus, preferably at least about 75%, more preferably at least about 85%, most preferably at least about 90%; at least about 50% of its flexural strength, preferably at least about 75%, more preferably at least about 80%, most preferably at least about 90%; at least about 50% of its tensile strength, preferably at least about 80%, more preferably at least about 90%, most preferably at least about 95%; at least about 50% of its shear strength, preferably at least about 75%, more preferably at least about 85%, most preferably at least about 95%; or a combination thereof.

In still another embodiment, upon exposure to PBS solution in vitro for about 36 weeks, an implantable medical device containing a poly(L-lactide-co-glycolide) copolymer according to the invention may retain: at least about 50% of its flexural modulus, preferably at least about 70%, more preferably at least about 80%, most preferably at least about 85%; at least about 50% of its flexural strength, preferably at least about 70%, more preferably at least about 80%, most preferably at least about 85%; at least about 50% of its tensile strength, preferably at least about 80%, more preferably at least about 90%, most preferably at least about 95%; at least about 50% of its shear strength, preferably at least about 85%, more preferably at least about 95%, most preferably at least about 99%; or a combination thereof.

In another embodiment, after 24 weeks of exposure to PBS solution in vitro, an implantable medical device containing a poly(L-lactide-co-glycolide) copolymer according to the invention may retain: at least about 25% of its flexural modulus, preferably at least about 40%, more preferably at least about 50%, alternately not more than about 80% or not more than about 65% or not more than 55%; at least about 10% of its flexural strength, preferably at least about 20%, also preferably at least about 40%, alternately not more than about 80% or not more than about 55% or not more than 25%; at least about 10% of its tensile strength, preferably at least about 20%, also preferably at least about 40%, alternately not more than about 80% or not more than about 55% or not more than 25%; at least about 10% of its flexural strength, preferably at least about 20%, also preferably at least about 40%, alternately not more than about 85% or not more than about 55% or not more than 25%; or a combination thereof.

The percent retention of the aforementioned mechanical properties or the aforementioned molecular weights is expressed herein either as a proportion based on the properties of the raw or as-purified poly(L-lactide-co-glycolide) copolymer or as a proportion based on the properties of the poly(L-lactide-co-glycolide) copolymer from the post-processed device; unless otherwise specified, mechanical property retention herein refers to the ratio of the particular mechanical property in the post-processed device to that same mechanical property in the exposed or implanted device.

composition ratio of about 80 mol % to about 10 mol % to about 10 mol %, respectively, was synthesized as Example 3. A terpolymer containing repeating units of L-lactide, D,L-lactide, and glycolide in a relative composition ratio of about 80 mol % to about 5 mol % to about 15 mol %, respectively, was synthesized as Example 4. A terpolymer containing repeating units of L-lactide, ε-caprolactone, and glycolide in a relative composition ratio of about 80 mol % to about 10 mol % to about 10 mol %, respectively, was synthesized as Example 5. Terpolymers such as those of Examples 1–5 can be obtained from various commercial suppliers, e.g., such as Purac Biochem. B.V., of Gorinchen, the Netherlands.

The molecular weights, inherent viscosities, raw melting points, and raw degrees of crystallinity for each of the terpolymers of Examples 1–5 are shown in Table 1 below. The compositions, as checked by $^1$H NMR and $^{13}$C NMR, for each of the terpolymers of Examples 1–5 are shown in Table 2 below.

TABLE 1

Copolymer Properties

| Example | Mw (g/mol) | Mn (g/mol) | polydispersity | Tm (° C.) | degree of crystallinity (%) | inherent viscosity (dL/g) |
|---|---|---|---|---|---|---|
| 1 | 1,639 k | 958 k | 1.7 | 137.5 | 25.8 | 6.5 |
| 2 | 1,246 k | 715 k | 1.7 | 131.7 | 19.8 | 5.3 |
| 3 | 946 k | 631 k | 1.5 | 134.5 | 24.6 | 4.4 |
| 4 | 1,435 k | 832 k | 1.7 | 136.1 | 24.7 | 6.0 |
| 5 | 639 k | 359 k | 1.8 | 134.4 | 22.6 | 3.3 |

TABLE 2

Confirmation of Copolymer Compositions by NMR

| Example | L-isomer content (mol %) | D-isomer content (mol %) | glycolide content (mol %)[1] |
|---|---|---|---|
| 1 | 89.6 | 5.4 | 4.8 (4.6) |
| 2 | 85 | 5 | 9.2 (7.6) |
| 3 | 84* | 6* | 10 (8.9) |
| 4 | 81.4** | 3.6** | 14.8 (15.6) |
| 5 | 81.6 | 9.2*** | 9.2 (6.6) |

[1]values in parentheses reflect $^{13}$C NMR analysis.
*thus, Example 3 contains 78 mol % L-lactide, 6 mol % D,L-lactide dimer (6% D-isomer plus 6% L-isomer), and 10% glycolide repeat units.
**thus, Example 4 contains 77.8 mol % L-lactide, 3.6 mol % D,L-lactide dimer (3.6% D-isomer plus 3.6% L-isomer), and 14.8% glycolide repeat units.
***Example 5 contains 9.2 mol % repeat units from ε-caprolactone monomer, not from D-isomers.

EXAMPLES

The preferred embodiments of the present invention will be illustrated by reference to the following examples, which are included to exemplify, but in no way limit, the scope of the present invention.

Examples 1–5

Copolymers According to the Invention and Properties Thereof

A terpolymer containing repeating units of L-lactide, D-lactide, and glycolide in a relative composition ratio of about 90 mol % to about 5 mol % to about 5 mol %, respectively, was synthesized as Example 1. A terpolymer containing repeating units of L-lactide, D-lactide, and glycolide in a relative composition ratio of about 85 mol % to about 5 mol % to about 10 mol %, respectively, was synthesized as Example 2. A terpolymer containing repeating units of L-lactide, D,L-lactide, and glycolide in a relative Examples 6–10

In Vitro Degradation Experiments on Terpolymers According to the Invention

Examples 6–10 correspond to exposure of samples of the terpolymers of Examples 1–5, respectively, to PBS solution at about 37° C. Samples of each terpolymer were analyzed after 4 weeks, 8 weeks, 12 weeks, 16 weeks, 20 weeks, 24 weeks, and 36 weeks exposure for their molecular weights and their mechanical and physical properties. These values are described below for each of Examples 6–10 in Tables 3–7, respectively.

TABLE 3

| Example 6 Property | Week 0 | Week 4 | Week 8 | Week 12 | Week 16 | Week 20 | Week 24 | Week 36 |
|---|---|---|---|---|---|---|---|---|
| Tm (° C.) | 143 | 142 | 142 | 143 | 145 | 144 | 145 | 148 |
| ΔHf (J/g) | 22 | 22 | 23 | 22 | 21 | 25 | 26 | 25 |
| deg. of crystal. (%) | 23 | 24 | 24 | 23 | 23 | 27 | 28 | 27 |
| Tg (° C.) | 58 | 58 | 58 | 57 | 55 | 55 | 56 | 55 |
| E(b) (GPa) | 8 | 7.6 | 8.2 | 8.1 | 8 | 7.9 | 7.4 | 7.1 |
| σ(b) (MPa) | 172 | 163 | 173 | 175 | 173 | 169 | 159 | 152 |
| σ(t) (MPa) | 135 | 136 | 147 | 149 | 148 | 144 | 137 | 134 |
| σ(s) (MPa) | 125 | 121 | 134 | 127 | 124 | 141 | 122 | 129 |
| Mn (g/mol) | 46,400 | 44,600 | 46,500 | 43,500 | 35,400 | | | |
| Mw (g/mol) | 118,000 | 116,000 | 116,000 | 108,000 | 96,500 | | | |
| I.V. (dL/g) | 2.5 | 2.5 | 2.5 | 2.4 | 2.2 | | | |

TABLE 4

| Example 7 Property | Week 0 | Week 4 | Week 8 | Week 12 | Week 16 | Week 20 | Week 24 | Week 36 |
|---|---|---|---|---|---|---|---|---|
| Tm (° C.) | 130 | 132 | 132 | 131 | 134 | 136 | 138 | 144 |
| ΔHf (J/g) | 16 | 16 | 18 | 16 | 20 | 22 | 23 | 24 |
| deg. of crystal. (%) | 17 | 17 | 19 | 17 | 22 | 23 | 24 | 25 |
| Tg (° C.) | 57 | 57 | 57 | 57 | 55 | 54 | 55 | 53 |
| E(b) (GPa) | 8.9 | 8.9 | 8.8 | 8.6 | 8.5 | 8.5 | 8.1 | 8.3 |
| σ(b) (MPa) | 198 | 197 | 193 | 186 | 187 | 183 | 177 | 176 |
| σ(t) (MPa) | 155 | 155 | 160 | 159 | 155 | 153 | 147 | 148 |
| σ(s) (MPa) | 124 | 125 | 131 | 137 | 130 | 142 | 126 | 134 |
| Mn (g/mol) | 43,000 | 41,800 | 36,000 | 28,000 | 17,600 | | | |
| Mw (g/mol) | 137,000 | 133,000 | 113,000 | 105,000 | 84,000 | | | |
| I.V. (dL/g) | 2.8 | 2.7 | 2.4 | 2.3 | 1.9 | | | |

TABLE 5

| Example 8 Property | Week 9 | Week 4 | Week 8 | Week 12 | Week 16 | Week 20 | Week 24 | Week 36 |
|---|---|---|---|---|---|---|---|---|
| Tm (° C.) | 136 | 138 | 140 | 142 | 144 | 144 | 144 | 136 |
| ΔHf (J/g) | 17 | 19 | 20 | 23 | 23 | 26 | 26 | 45 |
| deg. of crystal. (%) | 18 | 21 | 22 | 24 | 24 | 28 | 27 | 49 |
| Tg (° C.) | 56 | 56 | 54 | 55 | 55 | 50 | 49 | 42 |
| E(b) (GPa) | 8 | 7.4 | 7.3 | 7.5 | 7.5 | 7.7 | 4.9 | — |
| σ(b) (MPa) | 173 | 156 | 158 | 160 | 161 | 158 | 92 | — |
| σ(t) (MPa) | 147 | 134 | 136 | 136 | 141 | 132 | 75 | — |
| σ(s) (MPa) | 127 | 128 | 137 | 143 | 136 | 140 | 65 | 3 |
| Mn (g/mol) | 19,100 | 13,100 | 8,800 | 6,500 | 3,700 | | | |
| Mw (g/mol) | 66,700 | 49,700 | 33,900 | 25,400 | 16,800 | | | |
| I.V.(dL/g) | 1.6 | 1.3 | 1 | 0.8 | 0.6 | | | |

TABLE 6

| Example 9 Property | Week 0 | Week 4 | Week 8 | Week 12 | Week 16 | Week 20 | Week 24 | Week 36 |
|---|---|---|---|---|---|---|---|---|
| Tm (° C.) | 143 | 143 | 148 | 149 | 151 | 149 | 146 | 135 |
| ΔHf (J/g) | 18 | 19 | 21 | 22 | 23 | 26 | 27 | 46 |
| deg. of crystal. (%) | 19 | 21 | 22 | 24 | 25 | 28 | 29 | 50 |
| Tg (° C.) | 56 | 56 | 54 | 55 | 53 | 47 | 37 | 42 |
| E(b) (GPa) | 8.7 | 7.4 | 7.9 | 7.6 | 7.7 | 7.4 | 4.6 | — |
| σ(b) (MPa) | 197 | 165 | 177 | 179 | 170 | 160 | 48 | — |
| σ(t) (MPa) | 161 | 139 | 147 | 147 | 143 | 133 | 42 | — |
| σ(s) (MPa) | 130 | 136 | 143 | 143 | 147 | 143 | 34 | 2 |
| Mn (g/mol) | 28,700 | 16,100 | 7,500 | 5,000 | 2,900 | | | |
| Mw (g/mol) | 95,100 | 64,500 | 39,900 | 31,600 | 19,000 | | | |
| I.V. (dL/g) | 2.1 | 1.6 | 1.1 | 0.9 | 0.6 | | | |

TABLE 7

| Example 10 Property | Week 0 | Week 4 | Week 8 | Week 12 | Week 16 | Week 20 | Week 24 | Week 36 |
|---|---|---|---|---|---|---|---|---|
| Tm (° C.) | 133 | 141 | 144 | 139 | 139 | 135 | 132 | 125 |
| ΔHf (J/g) | 20 | 24 | 27 | 28 | 44 | 45 | 50 | 50 |
| deg. of crystal. (%) | 22 | 25 | 29 | 30 | 47 | 48 | 54 | 54 |
| Tg (° C.) | 44 | 44 | 40 | N/A | 38 | 39 | 34 | 37 |
| E(b) (GPa) | 7.4 | 5.2 | 2.9 | — | — | — | — | — |
| σ(b) (MPa) | 151 | 96 | 66 | — | — | — | — | — |
| σ(t) (MPa) | 129 | 67 | 40 | — | — | — | — | — |
| σ(s) (MPa) | 112 | 116 | 91 | 15 | 3 | — | — | — |
| Mn (g/mol) | 18,500 | 5,400 | 1,500 | 1,700 | 1,100 | | | |
| Mw (g/mol) | 65,300 | 23,400 | 5,800 | 6,600 | 4,300 | | | |
| I.V. (dL/g) | 1.6 | 0.7 | 0.3 | 0.3 | 0.2 | | | |

Examples 11–15

In Vitro Degradation Experiments on Terpolymers According to the Invention

Examples 11–15 correspond to exposure of non-sterilized samples of the terpolymers of Examples 1–5, respectively, to PBS solution at about 37° C. Samples of each terpolymer were analyzed after 1 week, 4 weeks, 8 weeks, and 12 weeks exposure for their mechanical properties. These values are described below for each of Examples 11–15 in Tables 8–12, respectively.

TABLE 8

| Example 11 Property | Week 0 | Week 1 | Week 4 | Week 8 | Week 12 |
|---|---|---|---|---|---|
| σ(t) (MPa) | 71 | 62 | 60 | 59 | 60 |
| σ(t) at break (MPa) | 71 | 52 | 56 | 54 | 56 |
| ε at break (mm/mm) | 0.035 | 0.047 | 0.028 | 0.03 | 0.029 |
| σ(t) at yield (MPa) | 49 | 46 | 47 | 46 | 45 |
| ε at yield (mm/mm) | 0.017 | 0.018 | 0.017 | 0.017 | 0.017 |
| E(b) (GPa) | 3.2 | 3 | 3.2 | 3.1 | 3.1 |

TABLE 9

| Example 12 Property | Week 0 | Week 1 | Week 4 | Week 8 | Week 12 |
|---|---|---|---|---|---|
| σ(t) (MPa) | 70 | 60 | 60 | 58 | 56 |
| σ(t) at break (MPa) | 62 | 50 | 55 | 52 | 55 |
| ε at break (mm/mm) | 0.041 | 0.049 | 0.03 | 0.033 | 0.028 |
| σ(t) at yield (MPa) | 49 | 45 | 44 | 44 | 41 |
| ε at yield (mm/mm) | 0.017 | 0.017 | 0.016 | 0.017 | 0.016 |
| E(b) (GPa) | 3.3 | 3 | 3.1 | 3 | 3 |

TABLE 10

| Example 13 Property | Week 0 | Week 1 | Week 4 | Week 8 | Week 12 |
|---|---|---|---|---|---|
| σ(t) (MPa) | 67 | 56 | 55 | 52 | 39 |
| σ(t) at break (MPa) | 62 | 48 | 52 | 49 | 39 |
| ε at break (mm/mm) | 0.032 | 0.045 | 0.027 | 0.026 | 0.019 |
| σ(t) at yield (MPa) | 48 | 43 | 43 | 41 | 36 |
| ε at yield (mm/mm) | 0.017 | 0.017 | 0.017 | 0.016 | 0.017 |
| E(b) (GPa) | 3.2 | 2.9 | 3.1 | 3 | 2.8 |

TABLE 11

| Example 14 Property | Week 0 | Week 1 | Week 4 | Week 8 | Week 12 |
|---|---|---|---|---|---|
| σ(t) (MPa) | 71 | 60 | 58 | 57 | 55 |
| σ(t) at break (MPa) | 65 | 51 | 56 | 56 | 54 |
| ε at break (mm/mm) | 0.035 | 0.067 | 0.026 | 0.028 | 0.025 |
| σ(t) at yield (MPa) | 49 | 43 | 44 | 43 | 43 |
| ε at yield (mm/mm) | 0.017 | 0.017 | 0.016 | 0.017 | 0.017 |
| E(b) (GPa) | 3.3 | 3.1 | 3.1 | 3 | 3 |

TABLE 12

| Example 15 Property | Week 0 | Week 1 | Week 4 | Week 8 | Week 12 |
|---|---|---|---|---|---|
| σ(t) (MPa) | 61 | 43 | 43 | 6 | |
| σ(t) at break (MPa) | 52 | 37 | 38 | 6 | |
| ε at break (mm/mm) | 0.033 | 0.03 | 0.027 | 0.005 | |
| σ(t) at yield (MPa) | 46 | 31 | 31 | 6 | |
| ε at yield (mm/mm) | 0.017 | 0.015 | 0.015 | 0.005 | |
| E(b) (GPa) | 3.1 | 2.5 | 2.5 | 1.5 | |

Although the present invention is described with reference to certain preferred embodiments, it is apparent that modification and variations thereof may be made by those skilled in the art without departing from the scope or this invention, particularly as defined by the appended claims.

What is claimed is:

1. An implantable medical device comprising a terpolymer having repeat units of L-lactide, D-lactide, and glycolide and that is made by the process comprising:
   contacting dimers or a combination of monomers and dimers that correspond to repeat unit structures of L-lactide, D-lactide, and glycolide to form a dimer or monomer-dimer mixture, wherein at least a portion of the L-lactide repeat units are supplied by L-lactide dimers or by L-lactic acid monomers;
   polymerizing substantially all of the dimer or monomer-dimer mixture to form the terpolymer.

2. The device of claim 1, which is fabricated into the form of a bone fixation plate, screw, tack, clip, staple, pin, rod, anchor, scaffold, sponge, implant for cell encapsulation, implant for tissue engineering, drug delivery device, monofilament or multifilament structure, sheet, membrane, and a foamed article.

3. The device of claim 1, wherein from about 1% to about 20% of the repeat units of the terpolymer are D-lactide repeat units.

4. The device of claim 3, wherein from about 4% to about 11% of the repeat units of the terpolymer are D-lactide repeat units.

5. The device of claim 1, wherein from about 50% to about 95% of the repeat units of the terpolymer are L-lactide repeat units.

6. The device of claim 5, wherein from about 75% to about 90% of the repeat units of the terpolymer are L-lactide repeat units.

7. The device of claim 1, wherein from about 1% to about 30% of the repeat units of the terpolymer are glycolide repeat units.

8. The device of claim 7, wherein from about 4% to about 18% of the repeat units of the terpolymer are glycolide repeat units.

9. The device of claim 1, wherein the terpolymer comprises from about 75% to about 90% L-lactide repeat units, from about 4% to about 11% D-lactide repeat units, and from about 4% to about 18% glycolide repeat units.

10. The device of claim 1, wherein the terpolymer consists essentially of about 85% L-lactide repeat units, about 5% D-lactide repeat units, and about 10% glycolide repeat units.

11. The device of claim 1, wherein the terpolymer consists essentially of about 90% L-lactide repeat units, about 5% D-lactide repeat units, and about 5% glycolide repeat units.

12. An implantable medical device comprising a terpolymer having repeat units of L-lactide, D,L-lactide, and glycolide and that is made by the process comprising:
contacting dimers or a combination of monomers and dimers that correspond to repeat unit structures of L-lactide, D,L-lactide, and glycolide to form a dimer or monomer-dimer mixture, wherein at least a portion of the L-lactide repeat units are supplied by L-lactide dimers or by L-lactic acid monomers;
polymerizing substantially all of the dimer or monomer-dimer mixture to form the terpolymer.

13. The device of claim 12, wherein the terpolymer comprises at least about 50% L-lactide repeat units, from about 1% to about 20% D,L-lactide repeat units, and from about 1% to about 30% glycolide repeat units.

14. The device of claim 12, wherein the terpolymer consists essentially of about 80% L-lactide repeat units, about 10% D,L-lactide repeat units, and about 10% glycolide repeat units.

15. The device of claim 12, wherein the terpolymer consists essentially of about 80% L-lactide repeat units, about 5% D,L-lactide repeat units, and about 15% glycolide repeat units.

16. An implantable medical device consisting essentially of a terpolymer having repeat units of about 80% L-lactide, about 10% ε-caprolactone, and about 10% glycolide and that is made by the process comprising:
contacting a combination of monomers and dimers that correspond to repeat unit structures of L-lactide, ε-caprolactone, and glycolide to form a monomer-dimer mixture; and
polymerizing substantially all of the monomer-dimer mixture to form the terpolymer.

17. The device of claim 1, wherein the terpolymer has a heat of fusion from about 0.5 J/g to about 15 J/g.

18. The device of claim 1, wherein the terpolymer has a heat of fusion from about 0.1 J/g to about 10 J/g.

19. The device of claim 1, wherein the terpolymer has a heat of fusion from about 15 J/g to about 25 J/g.

20. The device of claim 1, wherein the terpolymer has an inherent viscosity from about 2.5 dL/g to about 8 dL/g.

21. The device of claim 1, wherein the terpolymer has an inherent viscosity from about 4 dL/g to about 6.5 dL/g.

22. An implantable medical device comprising a terpolymer having repeat units depicted by the following formula:

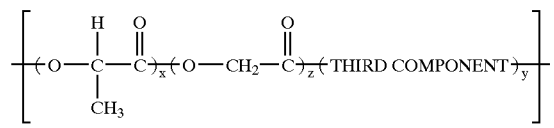

wherein the repeat unit having subscript x is an L-lactide repeat unit, the third component having subscript y is a D-lactide repeat unit; the molar percentages of the repeating units are such that x is from about 0.75 to about 0.9, y is from about 0.02 to about 0.16, and z is from about 0.04 to about 0.18; and x+y+z=1; and
wherein the terpolymer is made by the process comprising:
contacting dimers or a combination of monomers and dimers that correspond to repeat unit structures of L-lactide, glycolide, and either D-lactide or D,L-lactide, to form a dimer or monomer-dimer mixture, wherein at least a portion of the L-lactide repeat units are supplied by L-lactide dimers or by L-lactic acid monomers;
polymerizing substantially all of the dimer or monomer-dimer mixture to form the terpolymer.

23. The device of claim 22, wherein x is from about 0.75 to about 0.9, y is from about 0.04 to about 0.11, and z is from about 0.05 to about 0.15.

24. The device of claim 22, wherein x is essentially about 0.85, y is essentially about 0.05, and z is essentially about 0.1.

25. The device of claim 22, wherein x is essentially about 0.9, y is essentially about 0.05, and z is essentially about 0.05.

26. An implantable medical device comprising the terpolymer of claim 1 made by the process comprising:
combining L-lactide dimer, D-lactide dimer, and glycolide dimer to form a dimer mixture;
polymerizing substantially all of the dimer mixture to form the terpolymer.

27. An implantable medical device comprising the terpolymer of claim 12 made by the process comprising:
combining L-lactide dimer, D,L-lactide dimer, and glycolide dimer to form a dimer mixture;
polymerizing substantially all of the dimer mixture to form the terpolymer.

28. A terpolymer comprising from about 75% to about 90% L-lactide repeat units, from about 4% to about 11% D-lactide repeat units, and from about 4% to about 18% glycolide repeat units, wherein the terpolymer is made by the process comprising:
contacting dimers or a combination of monomers and dimers that correspond to repeat unit structures of L-lactide, D-lactide, and glycolide to form a dimer or monomer-dimer mixture, wherein at least a portion of the L-lactide repeat units are supplied by L-lactide dimers or by L-lactic acid monomers;
polymerizing substantially all of the dimer or monomer-dimer mixture to form the terpolymer.

29. The terpolymer of claim 28, which consists essentially of about 90% L-lactide repeat units, about 5% D-lactide at units, and about 5% glycolide repeat units.

30. The terpolymer of claim 28, which consists essentially of about 85% L-lactide repeat units, about 5% D-lactide repeat units, and about 10% glycolide repeat units.

31. A terpolymer comprising about 80% L-lactide repeat units, about 10% repeat units from ε-caprolactone, and about 10% glycolide repeat units, wherein the terpolymer is made by the process comprising:

contacting a combination of monomers and dimers that correspond to repeat unit structures of L-lactide, ε-caprolactone, and glycolide to form a monomer-dimer mixture;

polymerizing substantially all of the monomer-dimer mixture to form the terpolymer.

32. A terpolymer comprising at least about 50% L-lactide repeat units, from about 1% to about 20% D,L-lactide repeat units, and from about 1% to about 30% glycolide repeat units, wherein the terpolymer is made by the process comprising:

contacting dimers or a combination of monomers and dimers that correspond to repeat unit structures of L-lactide, D,L-lactide, and glycolide to form a dimer or monomer-dimer mixture, wherein at least a portion of the L-lactide repeat units are supplied by L-lactide dimers or by L-lactic acid monomers;

polymerizing substantially all of the dimer or monomer-dimer mixture to form the terpolymer.

33. The terpolymer of claim 32, which consists essentially of about 80% L-lactide repeat units, about 10% D,L-lactide repeat units, and about 10% glycolide repeat units.

34. The terpolymer of claim 32, which consists essentially of about 80% L-lactide repeat units, about 5% D,L-lactide repeat units, and about 15% glycolide repeat units.

* * * * *